United States Patent [19]

Dixon, Jr. et al.

[11] Patent Number: 5,534,243
[45] Date of Patent: Jul. 9, 1996

[54] AQUEOUS ORAL COMPOSITIONS

[75] Inventors: Cloyd Dixon, Jr., Covington, Ky.; Stephen J. Hunter-Rinderle, Mason, Ohio

[73] Assignee: The Procter & Gamble Company, Cincinnati, Ohio

[21] Appl. No.: 312,358

[22] Filed: Sep. 26, 1994

[51] Int. Cl.$^6$ .............................. A61K 7/16; A61K 31/30
[52] U.S. Cl. .............................. 424/49; 424/630; 514/499
[58] Field of Search .............................. 424/49–58, 630; 514/499

[56] References Cited

U.S. PATENT DOCUMENTS

| | | | |
|---|---|---|---|
| 3,164,524 | 1/1965 | Fand et al. | 167/93 |
| 4,154,815 | 5/1979 | Pader | 424/50 |
| 4,332,791 | 6/1982 | Raaf et al. | 424/49 |
| 4,339,429 | 7/1982 | Raaf et al. | 424/49 |
| 4,431,631 | 2/1984 | Clipper et al. | 424/53 |
| 4,540,567 | 9/1985 | Oneto et al. | 424/45 |
| 4,649,044 | 3/1987 | Gomi et al. | 424/49 |
| 4,661,342 | 4/1987 | Yamazaki et al. | 424/54 |
| 4,689,221 | 8/1987 | Kiyoshige et al. | 424/87 |
| 4,693,888 | 9/1987 | Miyahara et al. | 424/49 |
| 4,714,612 | 12/1987 | Nakamura et al. | 424/85 |
| 4,725,428 | 2/1988 | Miyahara et al. | 424/50 |
| 4,774,076 | 9/1988 | Gomi et al. | 424/49 |
| 4,816,261 | 3/1989 | Luebbe et al. | 424/65 |
| 4,824,661 | 4/1989 | Wagner | 424/52 |
| 4,897,261 | 1/1990 | Yamazaki et al. | 424/61 |
| 4,911,918 | 3/1990 | Kiyoshige et al. | 424/50 |
| 4,945,087 | 7/1990 | Talwar et al. | 514/60 |
| 4,954,335 | 9/1990 | Janchiprapanvej | 424/70 |
| 4,992,276 | 2/1991 | Dills et al. | 424/439 |
| 5,037,634 | 8/1991 | Williams et al. | 424/49 |
| 5,135,543 | 8/1992 | Chan et al. | 8/405 |
| 5,178,869 | 1/1993 | Ebine et al. | 424/401 |
| 5,211,940 | 5/1993 | Ishiguro et al. | 424/49 |
| 5,256,823 | 10/1993 | Chan et al. | 564/284 |
| 5,286,479 | 2/1994 | Garlich et al. | 424/54 |
| 5,292,527 | 3/1994 | Konopa | 424/54 |
| 5,298,237 | 3/1994 | Fine | 424/49 |
| 5,298,238 | 3/1994 | Hussein et al. | 424/49 |
| 5,389,360 | 2/1995 | Mobley, et al. | 424/49 |

FOREIGN PATENT DOCUMENTS

WO94/16674  8/1994  WIPO .............................. A61K 7/16

OTHER PUBLICATIONS

U.S. Ser. No. 08/096,535 filed Jul. 1993 Mobley et al.
U.S. Ser. No. 08/257,926 filed Jun. 1994 McLaughlin et al.
U.S. Ser. No. 08/258,151 filed Jun. 1994 McLaughlin et al.
U.S. Ser. No. 08/306,808 filed Sep. 1994 Shahidi.
U.S. Ser. No. 08/321,281 filed Oct. 1994 Mobley et al.

*Primary Examiner*—Shep K. Rose
*Attorney, Agent, or Firm*—Douglas C. Mohl; T. David Reed; Jacobus C. Rasser

[57] ABSTRACT

The present invention relates to aqueous oral compositions and methods of use providing improved antimicrobial activity and thereby reducing oral bacteria, mouth malodor and further promoting oral health.

11 Claims, No Drawings

AQUEOUS ORAL COMPOSITIONS

TECHNICAL FIELD

The present invention relates to aqueous oral compositions and methods of use providing improved activity and thereby reducing oral bacteria, mouth malodor and further promoting oral health.

BACKGROUND OF THE INVENTION

Dental plaque is a mixed matrix of bacteria, epithelial cells, leukocytes, macrophages and other oral exudate. Bacteria comprise approximately three-quarters of the plaque matrix. Any given sample of dental plaque could contain as many as 400 different varieties of microorganisms. This mix includes both aerobic and anaerobic bacteria, fungi and protozoa. Viruses have also been found in samples of dental plaque.

This matrix of organisms and oral exudate continues expanding and coalesces with other plaque growths situated nearby. The bacteria synthesize levans and glucans from sucrose found in the oral cavity providing energy for the microorganisms. These glucans, levans and microorganisms form an adhesive skeleton for the continued proliferation of plaque.

The bacteria found in plaque can secrete acids, enzymes and microtoxins which can cause caries, oral malodor and periodontal diseases such as gingivitis The use of mouthrinses to reduce or eliminate the bacterial flora of the oral cavity has been recognized for some time. Examples of previous references include: U.S. Pat. No. 4,994,262, Feb. 19, 1991 to Charbonneau et al.; U.S. Pat. No. 4,992,276, Feb. 12, 1991, to Dills et al.; U.S. Pat. No. 4,945,087, Jul. 31, 1990, to Talwar et al.; U.S. Pat. No. 4,923,685, May 8, 1990 to Wuelknitz et al.; U.S. Pat. No. 4,839,158, Jun. 13, 1989 to Michaels; U.S. Pat. 4,824,661, Apr. 25, 1989 to Wagner; U.S. Pat. No. 4,719,100, Jan. 12, 1988 to Frosch; U.S. Pat. 4,716,035, Dec. 29, 1987 to Sampathkumar; U.S. Pat. No. 4,606,911, Aug. 19, 1986 to Hayashi et al.; U.S. Pat. No. 4,525,343, Jun. 25, 1985 to Raaf; U.S. Pat. 4,323,551, Apr. 6, 1982 to Parran, Jr.; U.S. Pat. No. 4,312,889, Jan. 26, 1982 to Melsheimer; U.S. Pat. No. 4,152,418, May 1, 1979 to Pader; U.S. Pat. 4,082,841, Apr. 4, 1978 to Pader; U.S. Pat. No. 3,988,433, Oct. 26, 1976 to Benedict; U.S. Pat. No. 3,954,962, May 4, 1976 to Prussin; and U.S. Pat. 3,560,608, Feb. 2, 1971 to Griebstein et al.

In addition to the compositions set forth in the above-mentioned U.S. Patents, several additional references disclose mouthrinses for use in the oral cavity. See for example: Belgian Patent 776,425, published Jun. 8, 1972 to Imperial Chemical Industries Limited; Canadian Patent 1081-127, published Jul. 8, 1980; Japanese Kokai 54008-713, published Jan. 23, 1979; Japanese Kokai 49007-440, published Jan. 23, 1974; Soviet Union Patent 874-061, published Oct. 25, 1981 to Krasd Perfume Works and Soviet Union Patent Application 740-248, published Jun. 6, 1980 to Mosc Svoboda Cosmetics (similar to U.S. Pat. No. 3,591,675, Jul. 6, 1971 to Brillant).

While antimicrobials have long been used in oral compositions, there is still a need for improved aqueous oral compositions which provide, for example, improved antimicrobial activity along with increased user acceptance.

The present invention relates to aqueous oral compositions combining copper bis-glycinate and a surfactant to achieve improved antimicrobial activity.

It is therefore an object of the present invention to provide improved aqueous oral compositions. A still further object of the present invention is to provide an effective method of treating or preventing plaque and related periodontal diseases such as gingivitis.

These objects and other objects will become more apparent from the detailed description that follows.

SUMMARY OF THE INVENTION

The present invention relates to an aqueous oral composition comprising:

a.) a safe and effective amount of copper bis-glycinate;

b.) a surfactant; and c.) a pharmaceutically acceptable oral carrier wherein the compositions of the present invention contains less than 5%, and preferably less than 2%, ethyl alcohol. Preferably, the viscosity of the compositions is below about 5 centipoise.

The present invention further encompasses a method for treating diseases of the oral cavity using the specified aqueous oral compositions.

By "aqueous oral composition," as used herein, means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "pharmaceutically acceptable oral carrier," as used herein, means a suitable vehicle which can be used to apply the present compositions to the oral cavity in a safe and effective manner.

The pH of those compositions herein described range from about 4.0 to about 9.5, with the preferred pH being from about 4.0 to about 9.0 and the most preferred pH being 4.5 to about 8.5.

All levels and ratios are by weight of the total composition, unless otherwise indicated. Additionally, all measurements are made at 25° C. unless otherwise specified.

DETAILED DESCRIPTION OF THE INVENTION

The aqueous oral compositions of the present invention are preferably clear and include, but are not limited to, mouthrinses and sprays. By "clear" as used herein does not mean colorless, but means substantially lacking the presence of particles of sufficient size to scatter visible light as detected visually.

The essential as well as optional components of the compositions of the present invention are described in the following paragraphs.

ESSENTIAL INGREDIENTS

Copper bis-Glycinate

An essential component of the present invention is Copper bis-glycinate. Copper bis-glycinate is commercially available as the salt and has the structural formula:

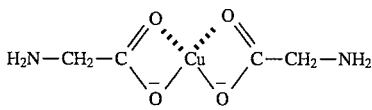

Copper bis-glycinate can also be formed in-situ by using appropriate salts of copper and glycine. Suitable copper compounds which supply copper ions are, in principle, all copper compounds being toxicologically harmless, compatible with mucous membranes and, to some extent, water-soluble.

The following inorganic copper salts may be used: Copper chloride, $CuCl_2$, and the dihydrate thereof; copper fluoride, $CuF_2$ and the dihydrate thereof, copper fluorosilicate, $CuSiF_6$, and the hexahydrate thereof; copper sulphate, $CuSO_4$, and the pentahydrate thereof; copper nitrate and the tri- and hexa-hydrates thereof, and also less popular copper salts, such as copper bromide, $CuBr_2$; copper metaborate, $Cu(BO_2)_2$; copper bromate $CU(BrO_3)_2$; copper chlorate; $Cu(ClO_3)_2$, $6-H_2O$; copper iodate $Cu(IO_3)_2$, and copper fluorophosphate, $CuPO_3F$.

Suitable sources of glycine besides glycine itself include sodium glycinate, potassium glycinate and glycine hydrochloride.

"Copper bis-glycinate" as the term is used herein includes ratios of copper and glycine differing somewhat from one part copper to two parts glycine. The ratios of copper to glycine which are most useful herein are as follows:

Preferred, about 1:1.5 to about 1:3.5;

More preferred, about 1:1.8 to about 1:3.0;

Most preferred, about 1:1.8 to about 1:2.4.

Copper bis-glycinate is used in an amount sufficient to provide from about 1 to about 8000, preferably from about 25 to about 6000, most preferably from about 50 to about 4000 ppm copper ions The rinses of the present invention preferably comprise from about 25 to about 1000 ppm, more preferably from about 50 to about 750 ppm, and most preferably from about 100 to about 500 ppm.

Surfactant

Another essential component of the present invention the surfactant. Surfactants (surface active agents) are organic compounds which reduce surface tension between liquids and aid in the dispersion of a composition throughout the oral cavity. Preferred surfactants include anionic surfactants, cationic surfactants, nonionic surfactants, betaines, zwitterionic surfactants or mixtures thereof. Suitable nonionic surfactants are described in U.S. Pat. No. 4,992,276, Feb. 12, 1991, Dills et al., incorporated herein by reference. Most preferred from among the nonionic surfactants are the poloxamer and ethoxylated hydrogenated castor oil surfactants. Particularly preferred from among the poloxamers is Poloxamer 407, which is sold under the tradename Pluronic F-127 by BASF-Wyandotte, Parsippany, N.J. Likewise preferred from among the ethoxylated hydrogenated castor oil surfactants is Cremophor RH40, which is also commercially available from BASF-Wyandotte, Parsippany, N.J.

Other nonionic surfactants useful in the present invention include condensates of sorbitan esters of fatty acids with ethylene oxide (polysorbates) such as sorbitan mono-oleate with from about 20 to about 60 moles of ethylene oxide (e.g., "Tweens," a trademark of ICI U.S., Inc.) Particularly preferred polysorbates are Polysorbate 20 (polyoxyethylene 20 sorbitan monolaurate, Tween 20) and Polysorbate 80 (polyoxyethylene 20 sorbitan mono-oleate, Tween 80).

Suitable anionic surfactants include the water soluble salts of alkyl sulfates having from 10 to 18 carbon atoms in the alkyl radical and the water-soluble salts of sulfonated monoglycerides of fatty acids having from 10 to 18 carbon atoms. Preferred for use are Sodium alkyl sulfate and sodium coconut monoglyceride sulfonates. Most preferred for use herein is sodium alkyl sulfate. Mixtures of anionic surfactants can also be utilized.

Additionally suitable anionic surfactants include those selected from the group consisting of sarcosinate surfactants, isethionate surfactants and taurate surfactants. Particularly preferred are the alkali metal or ammonium salts of these surfactants. Examples of this type include the sodium or potassium salts of the following: lauroyl sarcosinate, myristoyl sarcosinate, palmitoyl sarcosinate, stearoyl sarcosinate and oleoyl sarcosinate.

Betaine surfactants are also useful in the compositions of the present invention. Preferred betaine surfactants are disclosed in U.S. Pat. No. 5,180,577, Jan. 19, 1993, to Polefica et al., incorporated herein by reference. Typical alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramido propyl betaine.

Zwitterionic surfactants, like betaines, carry both a charged acidic and a charged basic moiety on the same molecule. Preferred zwitterionic synthetic surfactants can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Zwitterionic surfactants suitable for use in the present invention are further described in U.S. Pat. No. 4,198,392, Apr. 15, 1980, to Juneja, incorporated herein by reference.

The surfactant(s) is present in the compositions of the present invention preferably from about 0.1% to about 10%, more preferably from about 0.6% to about 2.0% and most preferably from about 0.6% to about 0.9%.

OPTIONAL COMPONENTS

Water can comprise from about 50% to about 90%, preferably from about 70% to about 85% of the compositions described herein. These amounts of water include the free water which is added, plus that amount which is introduced with other materials such as with sorbitol. Water, if used in the present invention, should preferably be deionized, distilled, free of organic impurities and bacteria and substantially free of metal ions.

Useful as optional components to the compositions of the present invention are polyhydric alcohols. Polyhydric alcohols are best known for their solvent and humectant properties. These alcohols are soluble in water, alcohols, ethers and lower aliphatic hydrocarbons and also act to solubilize the flavoring agents of the present invention. The polyhydric alcohols useful in the present invention include those selected from among the group consisting of propylene glycol, butylene glycol, hexylene glycol, polyethylene glycol and mixtures thereof.

The polyhydric alcohols can comprise from about 5% to about 30% of the inventive compositions, preferably from about 5% to about 20%.

Additionally, the present invention may optionally include a water-soluble fluoride compound present in the composition in an amount sufficient to give a fluoride ion concentration in the composition at 25° C. of from about 0.0025% to about 5.0% by weight, preferably from about 0.005% to about 2.0% by weight when it is used to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al., both being incorporated herein by reference. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Dental abrasives may also be optionally incorporated into compositions of the present invention. Typical dentally acceptable abrasives include insoluble calcium salts, alumina, silica, synthetic resins and mixtures thereof. Suitable silica abrasives are described in U.S. Pat. No. 5,176,900, herein incorporated by reference, and include both precipitated silicas and gel silicas. Preferred are the silica xerogels marketed under the tradename "Syloid" by W. R. Grace & Company, Davison Chemical Division. Preferred precipitated silica materials include those marketed by the J. M. Huber Corporation under the tradename "Zeodent", particularly the silica carrying the designation "Zeodent 119". Similarly, U.S. Pat. No. 4,623,536 discloses sodium bicarbonate, baking soda, as a mild abrasive and is herein incorporated by reference. Other compounds useful as abrasives are described in U.S. Pat. No. 5,176,901 which is also herein incorporated by reference. Mixtures of the above described abrasives may also be used.

Also desirable for inclusion in the compositions of the present invention are other stannous salts such as stannous gluconate and other antimicrobials such as bisbiquanide salts, quaternary ammonium compounds and nonionic antimicrobial salts. Also useful are enzymes, including endoglycosidase, papain, dextranase, mutanase and mixtures thereof. Such agents are disclosed in U.S. Pat. No. 2,946,725, July 26, 1960, to Norris et al. and U.S. Pat. No. 4,051,234, Sep. 27, 1977 to Gieske et al., both of which are herein incorporated by reference.

Another optional ingredient is a humectant. Humectants are well known in the art. The humectant may be a single agent or a mixture of compatible humectants In the present invention, suitable humectants include xylitol, glycerin and sorbitol as well as other polyhydroxy alcohols other than those mentioned above. While it is feasible to use a combination of humectants, the preferred embodiment incorporates the use of a single humectant. Humectants provide from about 0% to about 55%, and most preferably from about 5% to about 30% of the herein described invention. The preferred humectants include glycerin and/or sorbitol.

The flavoring agent or a mixture of compatible flavoring agents represent still another optional ingredient of the present invention. Such flavoring agents are well known in the art. Suitable flavoring agents include: anise, cassia, clove, dihydroanethole, estragole, menthol, peppermint, oxanone, phenyl ethyl alcohol, sweet birch, thymol, eugenol, eucalyptol, wintergreen, spearmint, cinnamic aidehyde, menthone, alpha-ionone, ethyl vanillin, limonene, isoamylacetate, benzaldehyde, ethylbutyrate and many others. In the herein described compositions the flavoring agents comprise from about 0.01% to about 5.0%, preferably from about 0.01% to about 2.0% and most preferably from about 0.04% to about 1.0% of the herein described composition.

Another preferred nonessential component of the present invention is a cooling agent or a combination of cooling agents. Suitable cooling agents are those described in U.S. Pat. No. 4,136,163, Jan. 23, 1979, to Watson et al., U.S. Pat. No. 4,230,688, Oct. 28, 1980, to Rowsell et al. and U.S. Pat. No. 4,032,661, to Rowsell et al., all of which are herein incorporated by reference. Particularly preferred cooling agents are N-ethyl-p-menthane-3-carboxamide (WS-3 supplied by Sterling Organics), taught by the above incorporated U.S. Pat. No. 4,136,163 and N,2,3-trimethyl-2-isopropylbutanamide which is commercially available as WS-23 from Wilkinson Sword Limited and taught by the above incorporated U.S. Pat. No. 4,230,688. Another particularly preferred cooling agent is 3-1-menthoxypropane 1,2-diol (TK-10 supplied by Takasago Perfumery Co., Ltd., Tokyo, Japan). This material is described in detail in U.S. Pat. No. 4,459,425, Jul. 10, 1984 to Amano et al. and incorporated herein by reference.

Other optional components include, but are not limited to: coloring agents; sweeteners, including saccharin, dextrose, levulose, cyclamate and aspartate, along with many others; buffering systems such as benzoic acid and sodium benzoate, citric acid and sodium citrate, bicarbonates, peroxides, nitrate salts such as sodium and potassium nitrate and any other buffering system compatible with the invention's herein described essential components. These agents, if present, are included at levels of from about 0.01% to about 30%.

EXAMPLES

The following examples further describe and demonstrate preferred embodiments within the scope of the present invention. The examples are given solely for illustration, and are not to be construed as limitation of this invention as many variations thereof are possible without departing from its spirit and scope.

Example I

A mouthrinse of the present invention is prepared by dissolving each of the following ingredients with agitation in a stainless steel or glass mixing tank:

| Ingredients | % W/W |
| --- | --- |
| Water, USP Purified | 68.1300 |
| Sorbitol (70% solution) | 30.0000 |
| Glycine | 0.0600 |
| Cupric sulfate, pentahydrate | 0.1000 |
| Sodium Saccharin | 0.0700 |
| PEG 40 hydrogenated caster oil[1] | 0.6000 |
| Flavor | 0.2400 |
| Sodium alkyl sulfate solution (27.9%) | 0.7500 |
| Sodium Hydroxide (50% solution) | 0.0500 |

[1]Available from BASF-Wyandotte, Parsippany, N.J. under the tradename Cremophor RH40.

Examples II–VII are combinations made by incorporating the components using conventional mixing technology similar to that described in Example I.

Example II

| Ingredients | % W/W |
| --- | --- |
| Water, USP Purified | 68.7400 |
| Sorbitol (70% Solution) | 30.0000 |
| Glycine | 0.0300 |
| Cupric sulfate, pentahydrate | 0.0500 |
| Sodium Saccharin | 0.0600 |
| PEG 40 hydrogenated caster oil[1] | 0.6000 |
| Flavor | 0.2400 |

-continued

| Ingredients | % W/W |
| --- | --- |
| Sodium alkyl sulfate solution (27.9%) | 0.2500 |
| Sodium Hydroxide (50% solution) | 0.0300 |

[1] Available from BASF-Wyandotte, Parsippany, N.J. under the tradename Cremophor RH40.

Example III

| Ingredients | % W/W |
| --- | --- |
| Water, USP Purified | 98.1300 |
| Glycine | 0.0600 |
| Cupric sulfate, pentahydrate | 0.1000 |
| Sodium Saccharin | 0.0700 |
| PEG 40 hydrogenated caster oil[1] | 0.6000 |
| Flavor | 0.2400 |
| Sodium alkyl sulfate solution (27.9%) | 0.7500 |
| Sodium Hydroxide (50% solution) | 0.0500 |

[1] Available from BASF-Wyandotte, Parsippany, N.J. under the tradename Cremophor RH40.

Example IV

| Ingredients | % W/W |
| --- | --- |
| Water, USP Purified | 68.5065 |
| Polysorbate 80 | 0.3000 |
| Sodium alkyl sulfate solution (27.9%) | 0.7500 |
| Sorbitol (70% solution) | 30.0000 |
| Flavor | 0.1600 |
| Glycine | 0.0600 |
| Cupric sulfate, pentahydrate | 0.1000 |
| Sodium Saccharin | 0.0700 |
| Sodium Hydroxide (50% solution) | 0.0535 |

EXAMPLE V

| Ingredients | % W/W |
| --- | --- |
| Water, USP Purified | 79.4065 |
| Polysorbate 80 | 0.2000 |
| Glycerin | 10.0000 |
| Butylene Glycol | 10.0000 |
| Flavor | 0.1200 |
| Glycine | 0.0600 |
| Cupric sulfate, pentahydrate | 0.1000 |
| Sodium Saccharin | 0.0600 |
| Sodium Hydroxide (50% solution) | 0.0535 |

Example VI

| Ingredients | % W/W |
| --- | --- |
| Water, USP Purified | 78.8565 |
| Sodium alkyl sulfate solution (27.9%) | 0.7500 |
| Polyethylene Glycol 600 | 10.0000 |
| Flavor | 0.1200 |
| Glycerin | 10.0000 |
| Glycine | 0.0600 |
| Cupric sulfate, pentahydrate | 0.1000 |
| Sodium Saccharin | 0.0600 |
| Sodium Hydroxide (50% solution) | 0.0535 |

Example VII

| Ingredients | % W/W |
| --- | --- |
| Water, USP Purified | 79.1925 |
| Polysorbate 80 | 0.2000 |
| Glycerin | 10.0000 |
| Hexylene Glycol | 10.0000 |
| Flavor | 0.1200 |
| Glycine | 0.1200 |
| Cupric sulfate, pentahydrate | 0.2000 |
| Sodium Saccharin | 0.0600 |
| Sodium Hydroxide (50% solution) | 0.1075 |

What is claimed is:

1. An aqueous oral composition comprising:

a.) a safe and effective amount of copper bis-glycinate;

b.) a surfactant;

c.) a polyhydric alcohol selected from the group consisting of propylene glycol, the polyethylene glycols, butylene glycol, hexylene glycol and mixtures thereof; and d.) a pharmaceutically acceptable carrier wherein the composition contains less than 5% ethyl alcohol.

2. A composition according to claim 1 wherein the concentration of the copper bis-glycinate is sufficient to provide from about 1 to about 8000 parts per million copper ions.

3. A composition according to claim 2 wherein the surfactant is selected from the group consisting of poloxamer surfactants, ethoxylated hydrogenated castor oil surfactants, sarcosinate surfactants, alkyl sulfate surfactants, sorbitan ester/ethylene oxide fatty acid condensates and mixtures thereof.

4. A composition according to claim 3 wherein the surfactant is selected from the group consisting of alkyl sulfate surfactants, ethoxylated hydrogenated castor oil surfactants and mixtures thereof.

5. A composition to claim 4 wherein said polyhydric alcohol is polyethylene glycol.

6. A composition according to claim 5 which further comprises from about 5.0% to about 55% of a humectant selected from the group consisting of glycerin, sorbitol and mixtures thereof.

7. A composition according to claim 6 wherein the cooling agent is selected form the group consisting of: 3-1-methoxypropane 1,2 -diol, N-ethyl-p-methane-3-carboxamide, N,2,3-trimethyl-2 -isopropylbutanamide and mixtures thereof.

8. A composition according to claim 7 wherein the viscosity of the composition is below about 5 centipoise.

9. A method of inhibiting bacteria, plaque and related periodontal diseases which comprises rinsing the oral cavity with a safe and effective amount of the composition of claim 1.

10. A method of inhibiting bacteria, plaque and related periodontal diseases which comprises rinsing the oral cavity with a safe and effective amount of the composition of claim 7.

11. A method of inhibiting bacteria, plaque and related periodontal diseases which comprises rinsing the oral cavity with a safe and effective amount of the composition of claim 8.

* * * * *